United States Patent [19]

Clemence et al.

[11] Patent Number: 4,501,740
[45] Date of Patent: Feb. 26, 1985

[54] BLOOD OXYGENATING AND CEREBRAL VASOREGULATING 20,21-DINOREBURNAMENINES

[75] Inventors: Francois Clemence, Paris; Italo Medici, Bondy; Robert Fournex, Paris; Colette Tournemine, Livry-Gargan, all of France

[73] Assignee: Roussel Uclaf, Paris, France

[21] Appl. No.: 420,791

[22] Filed: Sep. 21, 1982

[30] Foreign Application Priority Data

Oct. 8, 1981 [FR] France .................. 81 18935

[51] Int. Cl.³ .................. A61K 31/435; C07D 461/00
[52] U.S. Cl. ......................... 514/283; 546/51
[58] Field of Search ........................ 546/51; 424/256

[56] References Cited

U.S. PATENT DOCUMENTS

| | | | |
|---|---|---|---|
| 3,830,823 | 8/1974 | Castaigne | 546/51 |
| 3,937,709 | 2/1976 | Sevenet et al. | 546/51 |
| 4,033,969 | 7/1977 | Sevenet et al. | 546/51 |
| 4,120,858 | 10/1978 | Clauder et al. | 546/51 |
| 4,163,851 | 8/1979 | Clauder et al. | 546/51 |
| 4,291,038 | 9/1981 | Farcilli et al. | 424/256 |

FOREIGN PATENT DOCUMENTS 2475549 8/1981 France .
1568417 5/1980 United Kingdom .

Primary Examiner—Donald G. Daus
Assistant Examiner—Diana G. Rivers
Attorney, Agent, or Firm—Charles A. Muserlian

[57] ABSTRACT

Novel 20,21-dinoreburnamenines of the formula

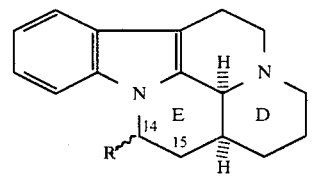

wherein R is selected from the group consisting of hydrogen, alkyl of 1 to 4 carbon atoms and $=CH_2$, the wavy line connecting to the E ring being a single bond when R is hydrogen or alkyl of 1 to 4 carbon atoms or a double bond when R is $=CH_2$ and the dotted line being possibly an endo carbon-carbon bond when R is hydrogen or alkyl of 1 to 4 carbon atoms and their non-toxic, pharmaceutically acceptable acid addition salts in all their possible isomers forms, racemic mixtures and optical isomers having oxygenating and cerebral vasoregulating activity of great value and a novel process and intermediates for their preparation.

21 Claims, No Drawings

BLOOD OXYGENATING AND CEREBRAL VASOREGULATING 20,21-DINOREBURNAMENINES

STATE OF THE ART

U.S. Pat. Nos. 4,163,851 and 4,120,858 and British Pat. No. 1,568,417 describe 20,21-dinoreburnamenines substituted in the 16-position with an ethyl group. French Pat. No. 2,475,549 describes 20,21-dinorebur- namenine substituted in the 14-position with the group

when $R_3$ is —OH, alkoxy of 2 to 4 carbon atoms or

and $R_5$ and $R_6$ may be hydrogen, alkyl of 1 to 4 carbon atoms and cycloalkyl of 3 to 6 carbon atoms.

STATE OF THE ART

It is an object of the invention to provide the novel compounds of formula I and their non-toxic, pharmaceutically acceptable acid addition salts and a novel process and intermediates for their preparation.

It is another object of the invention to provide novel blood oxygenating and cerebral vasoregulating compositions and to a novel method of blood oxygenating and cerebral vasoregulating activity in warm-blooded animals.

These and other objects and advantages of the invention will become obvious from the following detailed description.

THE INVENTION

The novel compounds of the invention are selected from the group consisting of 20,21-dinoreburnamenines of the formula

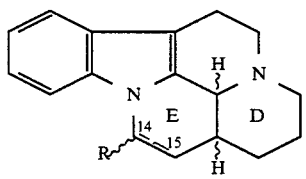

wherein R is selected from the group consisting of hydrogen, alkyl of 1 to 4 carbon atoms and =CH$_2$, the wavy line connecting to the E ring being a single bond when R is hydrogen or alkyl of 1 to 4 carbon atoms or a double bond when R is =CH$_2$ and the dotted line being possibly an endo carbon-carbon bond when R is hydrogen or alkyl of 1 to 4 carbon atoms and their non-toxic, pharmaceutically acceptable acid addition salts in all their possible isomers forms, racemice mixtures and optical isomers.

In the compounds of formula I, the hydrogens in the 3- and 16-positions can have either the α- or β-configuration which determines the existence of the cis and trans isomers. When R of formula I is alkyl, it is possible to have one of two possible configurations which results in the existence of 2 isomers. It is understood that mixtures of different isomers of formula I and especially mixtures of epimers of the 14-position when R is alkyl is within the scope of the invention.

Examples of R as alkyl are methyl, ethyl, n-propyl, isopropyl, n-butyl, isobutyl and tert.-butyl.

Examples of suitable acids for the formation of the non-toxic, pharmaceutically acceptable acid addition salts are inorganic acids such as hydrochloric acid, hydroiodic acid, hydrobromic acid, sulfuric acid, nitric acid and phosphoric acid and organic acids such as formic acid, acetic acid, protonic acid, benzoic acid, maleic acid, fumaric acid, succinic acid, tartaric acid, citric acid, oxalic acid, glyoxylic acid, aspartic acid, ascorbic acid, alkyl mono- and disulfonic acids such as methanesulfonic acid, ethanesulfonic acid, propanesulfonic acid, methane disulfonic acid and α,β-ethanedisulfonic acid and aryl mono- and disulfonic acids such as benzene sulfonic acid.

Among the preferred compounds of formula I are those wherein the hydrogens in the 3- and 16-positions are trans in all possible isomeric forms, racemates and optical isomers, those wherein the hydrogens in the 3- and 16-position are trans and the E-ring is saturated and R is hydrogen or alkyl of 1 to 4 carbon atoms in all possible isomeric forms, racemates and optical isomers and their non-toxic, pharmaceutically acceptable acid addition salts.

Specific preferred compounds of formula I are (3α,16β)14,15-dihydro-14-methyl-20,21-dinoreburenamenine, (3α,16β)14,15-dihydro-20,21-dinoreburnamenine, (3α,16β)-14-methyl-20,21-dinoreburenamenine and (3α,16β)20,21-dinoreburnamenine and their non-toxic, pharmaceutically acceptable acid addition salts.

The novel process of the invention for the preparation of the compounds of formula I and their acid addition salts comprises reacting a compound of the formula

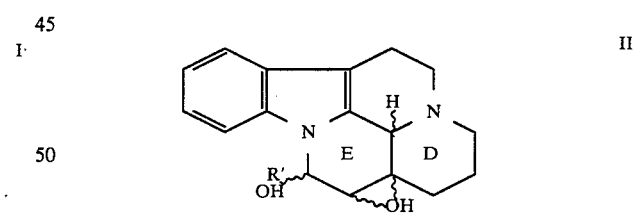

wherein R' is selected from the group consisting of hydrogen and alkyl of 1 to 4 carbon atoms with a dehydration agent to obtain a compound of the formula

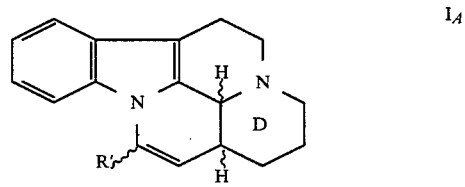

and isolating and salifying the latter if desired or a compound of the formula

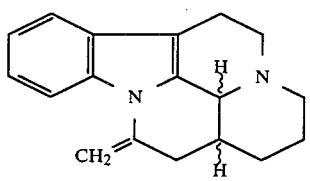

and isolating and salifying the latter if desired or reacting the compound of formula $I_A$ with a reducing agent to obtain a compound of the formula

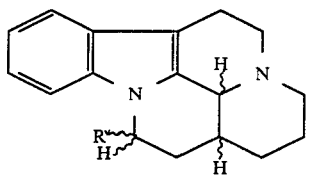

and isolating and salifying the latter if desired.

The compounds of formula II may be in the form of racemic mixtures or optical isomers and the resulting compounds of formula I will have the corresponding stereochemistry. The compounds of formula II may be used in their basic form or in their acid addition salt form and the product of formula I will be salified or not depending on the operating conditions.

The dehydration of the compound of formula II when R' is methyl results in a compound of formula I and the E ring has a double bond in 14–15 position and R is methyl or an isomer of a compound of formula I wherein the E ring does not have an endo double bond but R is $CH_2=$ in the 14-position or a mixture of the two isomers.

In a preferred mode of the process, the dehydration agent is an acid such as hydrochloric acid, hydrobromic acid, sulfuric acid, acetic acid, p-toluenesulfonic acid, methanesulfonic acid or a functional acid derivative such as the acid chloride and the reaction is effected in organic solvent such as toluene, xylene or tetrahydrofuran at a temperature from room temperature to reflux.

For dehydration of a compound of formula II wherein R' is methyl, the use of an anhydrous medium and an acid functional derivative yields a mixture of a compound of formula I wherein R is $=CH_2$ and its isomer where R is methyl and the E ring has an endo double bond in the 14–15 position and the 2 isomers may be separated by selective crystallization from an appropriate solvent, for example. When an acidic aqueous medium is used for dehydration, the major product is the compound of formula I wherein R is methyl and the E ring has an endo double bond.

Treating a compound of formula I wherein R is $=CH_2$ with an acid in an aqueous medium yields its isomer of formula I wherein R is methyl and the E ring has an endo double bond and examples of suitable acids are sulfuric acid, hydrochloric acid or phosphoric acid.

The reduction of a compound of formula $I_A$ is preferably effected with hydrogen in the presence of an catalyst such as palladium or platinum and it is effected in an organic solvent or mixtures thereof such as alcohols like ethanol, methanol or propanol or an ether such as ethyl ether, or tetrahydrofuran or an aromatic hydrocarbon such as toluene, benzene or xylene. The reaction may be effect at temperatures from $-20°$ C. to reflux, but preferably at room temperature.

The salification of the compounds of formula I may be effected in an organic solvent or mixtures thereof such s ethanol, tetrahydrofuran, acetone or ethyl acetate.

The optical isomers of formula I may be prepared directly by reacting the optical isomer of formula II or by resolution of racemic mixtures thereof by the usual means.

The blood oxygenating and cerebral vasoregulating compositions of the invention are comprised of blood oxygenating and cerebral vasoregulating effective amount of at least one compound of formula I and their non-toxic, pharmaceutically acceptable acid addition salts and an inert pharmaceutical carrier or excipient. The compositions may be in the form of tablets, dragees, gelules, granules, suppositories or injectable solutions or suspensions.

Examples of suitable excipients are talc, arabic gum, lactose, starch, magnesium stearate, cocoa butter, aqueous or non-aqueous vehicles, fatty bodies of animal or vegetable origin, paraffinic derivatives, glycols, diverse wetting agents, dispersants or emulsifiers and preservatives.

The compositions particularly increase the cerebral flow of blood by cerebral microcirculation and are useful for the treatment of cerebral vasculopathy and all symptoms caused by an alteration of cerebral circulation. They prevent or diminish the effects of cerebral arteriosclerosis, of cerebral circulatory troubles, of cerebral or meningea hemorraghes. They are particularly used in the treatment of cerebral insufficiencies, of cerebrovascular accidents and of cranial traumas.

Among the preferred compositions of the invention are those wherein the hydrogens in the 3- and 16-position are trans in all possible isomeric forms, racemates and optical isomers, those wherein the hydrogens in the 3- and 16-positions are trans and the E-ring is saturated and R is hydrogen or alkyl of 1 to 4 carbon atoms in all possible isomeric forms, racemates and optical isomers and their non-toxic pharmaceutically acceptable acid addition salts.

Specific preferred compounds of formula I are $(3\beta,16\alpha)14,15$-dihydro-14-methyl-20,21-dinoreburnamenine, $(3\beta,16\alpha)14,15$-dihydro-20,21-dinoreburnamenine, $(3\beta,16\alpha)$-14-methyl-20,21-dinoreburnamenine and $(3\beta,16\alpha)20,21$-dinoreburenamine and their non-toxic pharmaceutically acceptable acid addition salts.

The novel method of the invention for treatment of cerebral vascular disorders and cerebral syndroms provoked by an alteration or cerebral vascular circulation comprises administering to warm-blooded animals including humans an effective amount of at least one compound of formula I and their non toxic, pharmaceutically acceptable acid addition salts. The compounds may be administered, orally rectally or parenterally and the usual daily dose is 0.15 to 3 mg/kg depending on the condition treated, the compound used and the method of administration.

The compounds of formula II wherein R' is hydrogen are described in French Pat. No. 2,381,048 and the compounds of formula II wherein R' is alkyl of 1 to 4 carbon atoms are novel and a part of the invention. The latter compounds may be prepared by alkylating the corresponding 14-oxo compound which are known and may be prepared by the process of French Pat. No.

2,190,113 and Belgium Pat. No. 764,166. The alkylation may be effected with an alkyl magnesium halide in an organic solvent.

In the following examples there are described several preferred embodiments to illustrate the invention. However, it should be understood that the invention is not intended to be limited to the specific embodiments.

EXAMPLE 1

(3β,16α)20,21-dinoreburnamenine

A mixture of 2 g of (3β,16α)14,15-dihydro-20,21-dinoreburnamenine 14 ol (isomer with chemical displacement in the 14δ-position in 6.26 ppm), 25 ml of toluene and 0.002 g of p-toluene sulfonic acid was refluxed for 3½ hours and was evaporated to dryness under reduced pressure. The residue was taken up in 50 ml of boiling ethyl acetate and the solution was filtered. The filtrate was washed 3 times with 5 ml of ethyl acetate and evaporated to a volume of 15 ml under atmospheric pressure. The mixture was held at 18°–20° C. for one hour and was vacuum filtered. The product was washed with ethyl acetate at 20° C. and dried at 60° C. to obtain 1.4 g of (3β16α)20,21-dinoreburnamenine melting at 154° C.

Analysis: Calculated: %C 81.5; %H 7.24; %N 11.19. Found: 81.2; 7.4; 11.

NMR Spectrum (deuteropyridine): Peaks at 5 to 5.1 ppm (15-hydrogen); at 6.9 to 7.1 ppm (14-hydrogen); at 7 to 7.6 ppm (aromatic hydrogens); at 1 to 3 ppm (other hydrogens).

EXAMPLE 2

(3β,16α)14,15-dihydro-20,21-dinoreburnamenine

A mixture of 10 g of the compound of Example 1, 150 ml of methylene chloride and 1 g of 10% palladized active carbon was hydrogenated for 3½ hours and was then filtered. The filter was rinsed with methylene chloride and the filtrate was filtered through alumina and evaporated to dryness under reduced pressure. The 10.1 g of residue were empasted with stirring at 20°–25° C. with 50 ml of acetone for 30 minutes and the mixture was filtered. The product was rinsed with acetone to obtain 7.6 g of (3β,16α)14,15-dihydro-20,21-dinoreburnamenine melting at 132° C.

Analysis: Calculated: %C 80.90; %H 7.99; %N 11.10. Found: 81.0; 8.2; 10.9.

NMR Spectrum (deuteropyridine): Peaks at ≃3.42 to 4.4 ppm (2 hydrogens at the 14-position); at ≃7 to 7.7 ppm (aromatic hydrogens); at ≃1.08 to 2.08 ppm (ther hydrogens). Not absorption of wave length which indicates ethylenic hydrogens at 14–15 position.

EXAMPLE 3

(3β,16α)(±)14,15-dihydro-14-methylene-20,21-dinoreburnamenine

A mixture of 550 ml of 0.8M methyl magnesium bromide in tetrahydrofuran at 0° to 2° C. and a solution of 30 g of (3β,16α)(±)20,21-dinoreburnamenine-14(15H)one in 400 ml of tetrahydrofuran were mixed for 2 hours and the mixture was stirred for 5 hours while allowing the temperature to rise to 19° C. The mixture was stirred at 19° C. for 15 hours and was refluxed for 2½ hours. The mixture was cooled to 10° C. and slowly for 40 ml of acetyl chloride were added thereto over 100 minutes while keeping the temperature about 25° C. The mixture was stirred for 90 minutes and was then poured into one liter of aqueous saturated ammonium chloride solution containing 100 ml of concentrated ammonium hydroxide (pH>10). The decanted aqueous phase was extracted with ethyl acetate and the organic phase was washed with a 5N sodium hydroxide solution, dried and evaporated to dryness. The 44 g of residue were empasted with 100 ml of refluxing acetone for one hour and the mixture was cooled to 20° C. and vacuum fitered. The 9 g of residue melting at 146° C. was crystallized from ethanol to obtain 7.14 g of (3β,16α)(±)14,15-dihydro-14-methylene-20,21-dinoreburnamenine melting at 148° C.

Analysis: $C_{18}H_{20}N_2$ Calculated: %C 81,79; %H 7.62; %N 10.59. Found: 81.9; 7.7; 10.6.

NMR Spectrum (deuterochloroform): Peaks at 4.5 and 5.2 ppm ($CH_2=$); at 7.1 to 7.9 ppm (aromatic hydrogens); at 1 to 3.21 ppm (other hydrogens).

EXAMPLE 4

(3β,16α)14,15-dihydro-14-methyl-20,21-dinoreburnamenine 14 ol; HCl

A solution of 18 g of (3β,16α)±20,21-dinoreburnamenine-14(15H)one in 200 ml of tetrahydrofuran was added at 2° to 5° C. over one hour to 280 ml of 0.96N methyl magnesium bromide in tetrahydrofuran and after the temperature rose to room temperature, the mixture was stirred for 93 hours and then poured into 1.5 liters of an aqueous saturated ammonium chloride solution. The mixture was vacuum filtered and the product was washed with water and dried under reduced pressure at 60° C. to obtain 16.9 g of residue. 14.5 g of the residue were dissolved in 100 ml of dimethylformamide at 100° C. and the mixture was filtered. The filtrate was washed with 10 ml of hot dimethylformamide and stood for 3 hours at room temperature for crystallization and was vacuum filtered. The product was washed and dried at 60° C. to obtain 11.1 g of (3β,16α)14,15-dihydro-14-methyl-20,21-dinoreburnamenine 14-ol melting at 260° C. HPLC chromatography of the product showed the presence of 2 epimers at the 14-position with a 79%–21% ratio.

6 g of the said base were dissolved at 60° C. in 500 ml of dioxane and after cooling the mixture to 20° C., 2 ml of concentrated hydrochloric acid were added thereto. The mixture was stirred for 5 hours at room temperature and was filtered. The product was empasted with dioxane and then with ether and dried under reduced pressure at 60° C. to obtain 6 g of (3β,16α)14,15-dihydro-14-methyl-20,21-dinoreburnamenine-14-ol HCl. The latter was treated with N sodium hydroxide and dissolved in dioxane. A solution of hydrogen chloride in ethanol was added to the solution to effect precipitation and the mixture was filtered to obtain 4 g of the purified hydrochloride melting at 250° C.

Analysis: $C_{18}H_{23}N_2OCl$ Calculated: %C 67.81; %H 7.27; %N 8.78; %Cl 11.12. Found: 67.8; 7.3; 8.5; 10.9.

NMR Spectrum (dimethylsulfoxide): Peaks at 1.65 ppm (axial methyl); at 6.3 ppm (equatorial —OH); at 6.8 to 7.8 ppm (aromatic hydrogens).

EXAMPLE 5

(3β,16α)±14-methyl-20,21-dinoreburnamenine

The mother liquor remaining after recovery of the 9 g of product of Example 3 were evaporated to dryness and the residue was taken up in ether. The mixture was filtered and the filtrate was evaporated to dryness. The 30 g of oil were dissolved in 100 ml of ethyl acetate and 33 ml of an ethanolic 1.8N hydrogen chloride solution were added thereto at room temperature with stirring. The mixture which had a pH of 5 to 6 was stirred for 17 hours at room temperature and was vacuum filtered. The product was washed with ethyl acetate and dried at 60° C. under reduced pressure to obtain 13.7 g of raw (3β,16α)±14-methyl-20,21-dinoreburnamenine hydrochloride melting at 240°-260° C. 5.4 g of the product were dissolved in concentrated ammonium hydroxide and the solution was extracted with ether, dried and evaporated to dryness. The 4 g of residue were taken up in isopropyl ether and the solution was filtered. The product was dried and crystallized from petroleum ether to obtain 2 g of (3β,16α)±14-methyl-20,21-dinoreburnamenine melting at ≃100° C.

Analysis: $C_{18}H_{20}N_2$ Calculated: %C 81.78; %H 7.62; %N 10.59. Found: 81.7; 7.6; 10.5.

NMR Spectrum deuterochloroform): Peaks at 2.47 ppm

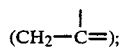

at 4.75 ppm (ethylenic hydrogen); at 7 to 7.7 ppm (aromatic hydrogens); at 1 to 3.3 ppm (other hydrogens).

EXAMPLE 6

(3β,16α)±14,15-dihydro-14-methyl-20,21-dinoreburnamenine

A mixture of 8.3 g of the product of Example 3, 600 ml of methanol and 1 g of platinum oxide was stirred at room temperature under a hydrogen atmosphere for 6 hours (889 ml of $H_2$ absorbed) and was then filtered. The filter was rinsed with methanol and the filtrate was evaporated to dryness under reduced pressure to obtain 8.5 g of raw (3β,16α)±14,15-dihydro-14-methyl-20,21-dinoreburnamenine. Analysis of the product by NMR Spectrum (dimethylsulfoxide) showed 2 isomers at 4.25 ppm which is an axial hydrogen at the 14-position (25% of product) and at 4.75 ppm which is equatorial hydrogen at the 14-position (75% of product).

The raw product was dissolved in 50 ml of ethanol and 12 ml of an ethanolic 1.8M hydrogen chloride solution were added thereto. The mixture was vacuum filtered and the crystals were empasted with ethanol and dried under reduced pressure at 60° C. to obtain 4.1 g of (3β,16α)±14,15-dihydro-14-methyl-20,21-dinoreburnamenine hydrochloride melting at >260° C.

Analysis: $C_{18}H_{23}N_2Cl$ Calculated: %C 71.39; %H 7.65; %Cl 11.71; %N 9.25. Found: 71.1; 7.8; 11.7; 8.9.

NMR Spectrum (DMSO): Not bands of adsorption corresponding to ethylenic hydrogens; peaks at 1.18-1.28 ppm ($CH_3$—CH=); at 4.25 ppm (3-hydrogen); at 4.75 ppm (equatorial 14-hydrogen); at 7 to 7.6 ppm (aromatic hydrogens).

EXAMPLE 7

Tablets were prepared containing 30 mg of (3β,16α)14,15-dihydro-14-methyl-20,21-dinoreburnamenine and sufficient excipient of lactose, treated starch, wheat starch, rice starch, talc and magnesium stearate for a final tablet weight of 150 mg.

Gelules were prepared containing 30 mg of said active ingredient and sufficient excipient of talc, aerosil and magnesium stearate for a final weight of 150 mg.

PHARMACOLOGICAL DATA

A. Hypobar anoxia test

Groups of 10 male mice weighing 20 to 22 g were starved for 5 hours and the mice received orally the test compound suspended in a solution of 0.5% methyl cellulose. 15 minutes later, the mice were placed in a 2 liter desiccator and the pressure was rapidly adjusted to 90 mm Hg with a pump to determine the survival time in seconds. The increase in the time of survival compared to that of the control animals under the same conditions are shown in Table I.

TABLE I

| Compound of Example | Dose in mg/kg | % increase in survival time |
|---|---|---|
| 2 | 50 | 106 |
| 2 | 10 | 20 |
| 4 | 50 | 32 |
| 5 | 25 | 59 |

B. Acute toxicity

The acute toxicity was determined as the $LD_0$ dose which is the maximum dose at which no mice died 8 days after orally receiving the test compound and the results are reported in Table II.

TABLE II

| Compound of Example | $LD_0$ in mg/kg |
|---|---|
| 2 | 200 |
| 3 | 600 |
| 4 | 200 |
| 5 | 100 |

Various modifications of the compounds and methods of the invention may be made without departing from the spirit or scope thereof and it is to be understood that the invention is intended to be limited only as defined in the appended claims.

What we claim is:

1. A compound selected from the group consisting of 20,21-dinoreburnamenines of the formula

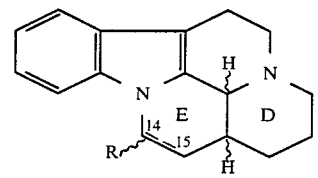

wherein R is selected from the group consisting of hydrogen, alkyl of 1 to 4 carbon atoms and =$CH_2$, the wavy line connecting to the E ring being a single bond when R is hydrogen or alkyl of 1 to 4 carbon atoms or a double bond when R is =$CH_2$ and the dotted line being possibly an endo carbon-carbon bond when R is hydrogen or alkyl of 1 to 4 carbon atoms and their non-toxic, pharmaceutically acceptable acid addition salts in all their possible isomers forms, racemic mixtures and optical isomers.

2. A compound of claim 1 wherein the hydrogens in the 3- and 16-position are trans.

3. A compound of claim 2 wherein the E ring is saturated and R is selected from the group consisting of hydrogen and alkyl of 1 to 4 carbon atoms.

4. A compound of claim 1 selected from the group consisting of (3β,16α)14,15-dihydro-14-methyl-20,21-dinoreburnamenine and its non-toxic, pharmaceutically acceptable acid addition salts.

5. A compound of claim 1 selected from the group consisting of (3β,16α)14,15-dihydro-20,21-dinoreburnamenine and its non-toxic, pharmaceutically acceptable acid addition salts.

6. A compound of claim 1 selected from the group consisting of (3β,16α)14-methyl-20,21-dinoreburnamenine and its non-toxic, pharmaceutically acceptable acid addition salts.

7. A compound of claim 1 selected from the group consisting of (3β,16α)20,21-dinoreburnamenine and its non-toxic, pharmaceutically acceptable acid addition salts.

8. A blood oxygenating and cerebral vasoregulating composition comprising a blood oxygenating and cerebral vasoregulating effective amount of at least one compound of claim 1 and a pharmaceutical carrier.

9. A composition of claim 8 wherein the hydrogens in the 3- and 16-position are trans.

10. A composition of claim 8 wherein the E ring is saturated and R is selected from the group consisting of hydrogen and alkyl of 1 to 4 carbon atoms.

11. A composition of claim 8 wherein the compound is selected from the group consisting of (3α,16β)14,15-dihydro-14-methyl-20,21-dinoreburnamenine and its non-toxic, pharmaceutically acceptable acid addition salts.

12. A composition of claim 8 wherein the compound is selected from the group consisting of (3α,16β)14,15-dihydro-20,21-dinoreburnamenine and its non-toxic, pharmaceutically acceptable acid addition salts.

13. A composition of claim 8 wherein the compound is selected from the group consisting of (3α,16β)14-methyl-20,21-dinoreburnamenine and its non-toxic, pharmaceutically acceptable acid addition salts.

14. A composition of claim 8 wherein the compound is selected from the group consisting of (3α,16β)20,21-dinoreburnamenine and its non-toxic, pharmaceutically acceptable acid addition salts.

15. A method of treatment of cerebral vascular disorders and cerebral syndromes provoked by an alteration of cerebral vascular circulation comprising administering to warm-blooded animals an effective amount of at least one compound of claim 1.

16. A method of claim 15 wherein the hydrogens in the 3- and 16-position are trans.

17. A method of claim 15 wherein the E ring is saturated and R is selected from the group consisting of hydrogen and alkyl of 1 to 4 carbon atoms.

18. A method of claim 15 selected from the group consisting of (3α,16β)14,15-dihydro-14-methyl-20,21-dinoreburnamenine and its non-toxic, pharmaceutically acceptable acid addition salts.

19. A method of claim 15 selected from the group consisting of (3α,16β)14,15-dihydro-20,21-dinoreburnamenine and its non-toxic, pharmaceutically acceptable acid addition salts.

20. A method of claim 15 selected from the group consisting of (3α,16β)14-methyl-20,21-dinoreburnamenine and its non-toxic, pharmaceutically acceptable acid addition salts.

21. A method of claim 15 selected from the group consisting of (3α,16β)20,21-dinoreburnamenine and its non-toxic, pharmaceutically acceptable acid addition salts.

* * * * *